United States Patent [19]

Shinpo et al.

[11] Patent Number: 4,581,217
[45] Date of Patent: Apr. 8, 1986

[54] PROCESS FOR PREPARING SILICA BASE FOR DENTIFRICE

[75] Inventors: Shozo Shinpo, Hyogo; Tetsuo Fushino, Takasago; Akihiro Hachijo, Kobe; Shozo Ohtsu, Kakogawa, all of Japan

[73] Assignee: Taki Chemical Co., Ltd., Hyogo, Japan

[21] Appl. No.: 667,487

[22] PCT Filed: Feb. 28, 1984

[86] PCT No.: PCT/JP84/00071
§ 371 Date: Oct. 17, 1984
§ 102(e) Date: Oct. 17, 1984

[87] PCT Pub. No.: WO84/03439
PCT Pub. Date: Sep. 13, 1984

[30] Foreign Application Priority Data

Mar. 8, 1983 [JP] Japan .................................. 58-38806

[51] Int. Cl.$^4$ .............................................. C01B 33/18
[52] U.S. Cl. ...................................................... 423/339
[58] Field of Search ......................................... 423/339

[56] References Cited

U.S. PATENT DOCUMENTS 3,893,840  7/1975  Wason ................................. 423/339
4,038,098  7/1977  Wason ................................. 423/339

Primary Examiner—Jack Cooper
Attorney, Agent, or Firm—Wenderoth, Lind & Ponack

[57] ABSTRACT

Silica base material for dentifrice having excellent transparency, prolonged stability and desired abrasiveness, has specific surface areas measured by BET method and CTAB method of 5–60 m$^2$/g respectively with a difference therebetween of less than 40 m$^2$/g, and having a refractive index of 142–1.45. This base material can be prepared by reacting an alkali metal silicate solution with hydrochloric acid or sulfuric acid in the presence of an electrolyte in two stages, a silica crystallization stage in which the pH of the reaction system is brought to 10.0, and a neutralization stage in which the pH of the reaction system is brought to 8.0–6.5, completing the neutralization stage within 30 minutes and aging the neutralized mixture for at least 10 minutes. The ratio of the rate of addition of chloride or sulfate ions between the neutralization and crystallization stages is at least 5:3.

9 Claims, No Drawings

PROCESS FOR PREPARING SILICA BASE FOR DENTIFRICE

TECHNICAL FIELD

This invention relates to a silica base material for dentifrice formulation, particularly to one for transparent dentifrice formulation, which gives an outstanding, stable transparency yet with a desired abrasiveness.

BACKGROUND ART

Of late years transparent dentifrice formulations of various types have been developed and put on the market, giving a favorable impression with their freshness and cleanliness associated with the transparency.

For transparent dentifrice formulations there has been used in the past a silica base material which can impart transparency to the dentifrice formulation, but has no substantial abrasiveness so that the resulting dentifrice has not been satisfactory in actual use as a dentifrice. Further, it has also been proposed to use a silica base material which has a refractive index which is close to that of the transparent dentifrice vehicle used for formulation into a transparent dentifrice, but the known silica base material has a refractive index that shows fluctuation and is poor in stability so that it is difficult to obtain a transparent dentifrice with good stability.

Meanwhile, several methods have been proposed to produce silica base materials having appropriate abrasiveness for transparent formulation. For example, Japanese Pat. Publication No. '74-11159 describes a method wherein a commercial super-fine amorphous silica devoid of abrasiveness and therefore unsuitable for dentifrice base material is wetted with water or a dilute aqueous solution of inorganic alkali metal salt, fired at 500-1000° C., and then ground. It is true that this method provides abrasiveness needed by a dentifrice base material. But the abrasiveness thus provided is often so much in excess as to damage tooth enamel and the material itself does not give good transparency and consistent stability. Finally, it would be hard to industrialize the method economically.

Another method is described in Japanese Pat. Kokai Nos. '76-12869 and '76-136841 to provide abrasiveness to silica. The material obtained by this method, however, does not give good paste stability when combined with a transparent dentifrice vehicle.

The invention described in Japanese Pat. Publication No. '73-14935 discloses a transparent dentifrice formulation containing silica specified as follows:

Refractive index: 1.40-1.47
oil absorption: 1.5 cc and less
particle size: ca. 0.01-0.5μ

The silica prepared by the method disclosed in this publication gives a BET surface area of 150 m²/g, and a CTAB surface area of 82 m²/g. When this silica is mixed with humectant and left to stand, the turbidity of the mixture, or paste, grows markedly from day to day and the paste stability is gradually worsened.

In addition, one of the present inventors disclosed in Japanese Pat. Publication Nos. '74-8640 and '77-15078 a method to control the refractive index of silica by allowing fluoride ion to intervene in the proposed process. The product of this invention as a base material for transparent dentifrice formulation was still not without a problem in transparency and was not as stable as expected.

Thus the silicas publicly known heretofore have defects either in abrasiveness, stability or transparency which are the essential characteristics of the base material for transparent dentifrice formulation, and therefore none of them are satisfactory for such formulation.

Years of intensive study on these essential characteristics of silica base material has now revealed to the present inventors that combinations of a toothpaste vehicle with the silica base material of the present invention, as described in detail below, can bring forth a transparent dentifrice formulation with proper abrasiveness, water-like transparency and good long-term stability under storage.

Transparency as referred to in this invention is defined and measured as follows: two solutions of different refractive indices like glycerine and water are mixed in various proportions to give dispersion media of different refractive indices; a fixed amount of silica base material is then mixed with a fixed amount of each medium into a dispersion, which, as needed, is deaerated and subjected to measurement of refractive index and turbidity; and with these as parameters a curve is plotted to determine the minimum turbidity point which represents the transparency here.

The present inventors studied in detail the factors influencing the transparency and, finding that the porosity of silica base material is greatly involved, came to accomplish the invention.

DISCLOSURE OF THE INVENTION

Namely, the invention relates to a silica base material for dentifrice formulation characterized by having a specific surface area by the BET method of 5-60 m²/g-anhydride, and by the CTAB method of 5-60 m²/g-anhydride; having a difference in specific surface area of less than 40 m²/g-anhydride between the BET method and the CTAB method; and having a refractive index of 1.42-1.45.

Now before proceeding further, explanations will be given here on the terminology covering specific surface area by the BET method, specific surface area by the CTAB method, refractive index and loss by abrasion, or abrasiveness.

(1) Measurement of specific surface area by the BET method. With liquid nitrogen as coolant, the adsorption in quantity of nitrogen gas by sample is measured at $-196°$ C.; the surface area per one gram of sample in anhydride form is then calculated, based on the molecular cross-section of nitrogen, $16.2 Å^2$. Deaeration of the sample is conducted at 140° C. under vacuum of $1 \times 10^{-5}$ mmHg for 60 minutes.

(2) Measurement of specific surface area by the CTAB method. Cetyl methyl ammonium bromide is allowed to be adsorbed onto the sample until saturation from its aqueous solution; the surface area per gram of sample in anhydride form is then calculated, based on the molecular cross-section of the bromide, $35Å^2$.

Procedure: Take 1 g of sample of known moisture content in a 300 ml conical flask having a common stopper. Add 100 ml of 0.55% solution of CTAB and bring the pH of the mixture to 9.0 with 0.1N NaOH solution. Keep agitating for 2 hours with a magnetic stirrer. Settle the suspension centrifugally and transfer 10 ml of the supernatant into a 300 ml conical flask. Add 50 ml of demineralized water, 25 ml of chloroform, drops of bromophenol blue indicator and titrate it with sodium dioctyl sulfo succinta (Aerosol OT) solution previously calibrated by a standard CTAB solution. End the titration when the chloroform layer is decolorized while the aqueous layer is slightly tinged purple. Make the consumption in ml of Aerosol OT as $V_2$.

Then conduct a blank titration in a similar manner on 10 ml of the first CTAB solution only and mark the Aerosol OT consumption in ml as $V_1$.

Calculate the surface area per gram of anhydrate ($Sm^2/g$) by the following equation.

$$S = \frac{5.78 \times (V_1 - V_2) \times a}{X}$$

Wherein
X = sample weight as anhydrate (g);
a = CTAB in weight (mg) equivalent to 1 ml of the Aerosol OT solution (3) Refractive index Mix glycerine and water in various proportions to obtain dispersing media of different refractive indices. Disperse 15 g of sample in 35 g of each medium using a vacuum mortar-mixer for 10 minutes.

Measure the refractive index and turbidity of the mixture at 25° C. and plot the data to obtain a refractive index-turbidity curve. Represent the sample by the refractive index of the mixture at the lowest turbidity point. In these measurement use an Abbe's refractometer and an integration sphere turbidimeter; and determine turbidity from the transmittancy at sample thickness of 1 mm.

(4) Abrasiveness

Use an abrasion tester of horizontal brushing movement; of a suspension of 25% silica fine powder in 60% glycerine/water solution, take some and put it on the flat face of the bronze plate; with the testing load, or weight of 500 g on it, conduct the brushing 18,000 times; then measure the weight loss of the bronze plate for abrasiveness. The word "anhydride" as used in this invention shall refer to a form or state of finely ground silica dried up to nearly constant weight at 105° C. for two hours.

Now the method for making the silica base material for dentifrice formulation of this invention will be described in detail.

The alkali metal silicate used in the invention includes sodium, potassium and lithium silicate, but more preferred of these is sodium silicate because it is less costly. Silicates having a molar ratio, $SiO_2/X_2O$, (wherein X denotes alkali metal,) of 2-4 can be used. The acidifying agent used in this invention is hydrochloric or sulfuric acid.

The preferably $SiO_2$ concentration of the alkali metal silicate solution at the stage of acidification with such acid is 5-15% by weight and the preferable acid concentration is also 5-15% by weight; and in proper combination with other reaction parameters the acid and silicate concentrations within such ranges can bring forth the desired properties of silica base material.

The electrolytes preferred in this invention are alkali metal salts of mineral acid such as sodium chloride, potassium chloride, sodium sulfate, potassium sulfate, sodium carbonate, potassium carbonate, sodium nitrate and potassium nitrate, to name only sodium and potassium salts as typical examples. The electrolyte is used in the range of 10-60% by weight of $SiO_2$, as required, considering the abrasiveness of silica base material.

In the present invention the alkali metal silicate solution is first made to react with hydrochloric or sulfuric acid under the presence of such electrolyte.

The preferred manner of performing the reaction is to mix the electrolyte previously with the alkali metal silicate solution, in view of giving the abrasiveness to silica base material. However, it is also acceptable to add the electrolyte, in consideration of its quantity, reaction temperature, reaction time, etc., to hydrochloric or sulfuric acid in advance. In said preferred manner also it is well to charge the reactor with alkali metal silicate solution and electrolyte solution simultaneously or separately, or it is as well to mix these two solutions prior to their introduction into the reactor.

It is preferable to conduct the reaction under good agitation in a temperature range of 60-100° C.

The essence of the production method of silica base material disclosed herein lies in the fact that the reaction is conducted in two stages;- the silica crystallization stage for which the pH of the reaction mixture is brought to 10.0, and the neutralization stage for which the pH is finally brought down to 8.0-6.5; the ratio of the rate of addition of chloride or sulfate ion between said two stages is at least 5:3; and the neutralization is carried out within 30 minutes, and the ageing should be performed for at least 10 minutes.

The silica crystallization stage herein means the stage of reaction where more than 95% of silica content (as $SiO_2$) in the alkali metal silicate solution is crystallized out. It is preferable to conduct this part of the reaction to take 40 minutes to 4 hours.

Meanwhile, the neutralization stage is the stage of reaction ranging from the point where most of the silica has neutralized out at the reaction pH of 10.0 to the point where the pH has been brought down to 8.0-6.5 by adding hydrochloric or sulfuric acid. Taking too long in the neutralization or taking too short in the ageing somehow makes it difficult to obtain silica base material of excellent and long-lasting transparency and good abrasiveness.

The present inventors, therefore, studied further for a method devoid of such a defect, which would give a variety of silica base material of low to high abrasiveness for transparent formulation, and found that it is necessary to perform the neutralization stage within 30 minutes and that the ratio of the rate of addition of hydrochloric or sulfuric ion between the neutralization and silica crystallization stages should be at least 5:3, and also the ageing should be performed for at least 10 minutes. Namely, shortening the neutralization stage and at least 10 minutes ageing led to remarkable improvements in the characteristics of silica base material and its productivity.

When the pH reaction mixture in the neutralization stage is made 8.0-6.5, the refractive index of the resulting silica base material can be brought within a narrow range of 1.42-1.45. When the reaction pH is below 6.5, good silica base material for transparent formulation can not be obtained because of the scattering of refractive indices. When the reaction pH exceeds 8.0, turbidity on refractive index is carried too high, and also it makes the pH of the silica base too high, and therefore is not good for the silica base material for a dentifrice.

The rest of the operation is to filter, wash, dewater, dry and grind the silica base material in the usual manner.

The silica base material thus obtained has a specific surface area by the BET method of 5-60 $m^2/g$-anhydride and also one by the CTAB method of 5-60 m$^2$/g-anhydride; having the difference in specific surface area of less than 40 m$^2$/g-anhydride between the BET method and the CTAB method; and having a refractive index of 1.42-1.45. The product shows good transparency and a long-term stability. The abrasiveness of the product can be changed freely within the range of 2-90 mg. Thus the product is a useful base material particularly for transparent dentifrice formulations.

Described above is one of the processes for producing silica base material for transparent dentifrice formulations, and it is also possible to obtain by a different process silica base material having a specific surface area by the BET method of 5-60 m$^2$/g-anhydride and also one by the CTAB method of 5-60 m$^2$/g-anhydride, having the difference in specific surface area of less than 40 m$^2$/g-anhydride between the BET method and the CTAB method.

It is clear that the thus obtained base material has excellent transparency and stability over time. Furthermore, in the production of the silica herein, it is, of course, possible to use and add, for the purpose of adjusting abrasiveness or as refractive index controlling agent, to the alkali metal silicate solution, hydrochloric acid or sulfuric acid and others, or while in the reaction stage, aluminum sulfate, aluminum chloride, calcium chloride, magnesium chloride, basic salts of these compounds, sodium fluoride, potassium fluoride, ammonium fluoride and others.

Now, the features of silica base material for dentifrice formulations of this invention will be better clarified through the examples shown below:

REFERENCE 1

Into a 20 l reactor equipped with a baffle plate and an agitator with 150 mm D turbine blades was introduced 10 kg of an aqueous solution of sodium silicate (Na$_2$O.3.2 SiO$_2$) containing 110 g/kg of SiO$_2$ and then, under the reaction temperature kept at 75° C., 11% sulfuric acid at the flow rate of 57 g/min for 63 minutes to bring the pH of reaction mixture to 10.0. Then the addition of 11% sulfuric acid was continued at the flow rate of 96 g/min until 12 minutes later when the pH reached 7.8. The acid was stopped and the reaction mixture was allowed to stand for ageing for 20 minutes. After repeated filtration and washing, the obtained solid was dried in a hot air oven at 110° C. and finely ground.

The fine silica powder thus obtained has a specific surface area by the BET method of 171 m$^2$/g and by the CTAB method of 146 m$^2$/g; and the difference in specific surface area between both methods was 25 m$^2$/g.

The fine silica powder thus obtained had good transparency as a base material for transparent dentifrice formulation, but a poor abrasiveness, and when it was used for toothpaste, increased the viscosity. Thus, silica of this kind was found not to be usable for toothpaste in its preparation.

REFERENCE 2

Into a reactor used in reference 1 was introduced 10 kg of an aqueous solution of sodium silicate (Na$_2$O.3.1 SiO$_2$) containing 90 g/kg of SiO$_2$ and 11 g/kg of NaCl and then, under the reaction temperature kept at 65° C., 9% sulfuric acid at the flow rate of 176 g/min for 21 minutes to bring the pH of the reaction mixture to 10.0. Then the addition of 9% sulfuric acid was continued at the flow rate of 32 g/min until 46 minutes later when the pH reached 5.8. Acid addition was stopped and the mixture was then allowed to stand for ageing for 30 minutes. After repeated filtration and washing, the wet cake was dried in a hot air oven at 110° C. and finely ground.

The fine silica powder thus obtained had a specific surface area by the BET method of 215 m$^2$/g and by the CTAB method of 98 m$^2$/g; and the difference in specific surface area was 117 m$^2$/g. This silica has poor abrasiveness, comparatively high turbidity and poor long-lasting transparency, thus not being suitable for transparent dentifrice formulation as base material.

REFERENCE 3

Into a reactor used in reference 1 was introduced 10 kg of an aqueous solution of sodium silicate (Na$_2$O.2.7 SiO$_2$) containing 100 g/kg of SiO$_2$ and 25 g/kg of NaCl and then, under the reaction temperature kept at 80° C., 10% sulfuric acid at the flow rate of 46 g/min for 95 minutes to bring the pH of reaction mixture to 10.0. Then the addition of 10% sulfuric acid was continued at the flow rate of 92 g/min until 17 minutes later when the pH reached 6.2. The acid was stopped and the reaction mixture was filtered immediately. After repeated filtration and washing, the obtained solid was dried in a hot air oven at 110° C. and finely ground.

The fine silica powder thus obtained had a specific surface area by the BET method of 83 m$^2$/g and by the CTAB method of 18 m$^2$/g; and the difference in specific surface area was 65 m$^2$/g. This silica had comparatively high abrasiveness as base material for dentifrice formulations, but the product made from this silica showed high turbidity and poor long-lasting transparency, and thus, this silica is not of such quality as can be used for transparent toothpaste as base material.

REFERENCE 4

Into a reactor used in reference 1 was introduced 10 kg of sodium silicate solution (Na$_2$O.3.1 SiO$_2$) containing 95 g/kg of SiO$_2$ and 35 g/kg of NaCl and then under the reaction temperature kept at 95° C., 10% sulfuric acid at the flow rate of 56 g/min for 89 minutes to bring the pH of the reaction mixture to 5.2. The acid was stopped and the reaction mixture was allowed to stand for ageing for 15 minutes. After repeated filtration and washing, part of the wet cake was dried in a hot air oven at 110° C. and finely ground.

The fine silica powder thus obtained had a specific surface area by the BET method of 208 m$^2$/g and by the CTAB method of 21 m$^2$/g; and the difference in specific surface area was 187 m$^2$/g.

This silica base material prove to be a product of sufficient abrasiveness to meet requirements of base material for toothpaste but of high turbidity and giving poor transparency over time, and is not suited for silica base material for transparent dentifrice formulation.

REFERENCE 5

Into a reactor used in reference 1 was introduced 10 kg of an aqueous solution of sodium silicate (Na$_2$O.3.2 SiO$_2$) containing 100 g/kg of SiO$_2$ and 17.5 g/kg NaCl and then, under the reaction temperature kept at 85° C., 10% sulfuric acid at the flow rate of 36 g/min for 100 minutes to bring the pH of reaction mixture to 10.0. The addition of 10% sulfuric acid was continued at the flow rate of 26 g/min until 52 minutes later when the pH reached 6.3. The acid was stopped and the reaction mixture was allowed to stand for ageing for 30 minutes.

After repeated filtration and washing, the obtained solid was dried in a hot air oven at 110° C. and finely ground.

The fine silica powder thus obtained had a specific surface area by the BET method of 59 m$^2$/g and by the CTAB method of 16 m$^2$/g; and the difference in specific surface area was 43 m$^2$/g. This silica base material proved to be a product of sufficient abrasiveness to meet requirements of base material for toothpaste but giving poor transparency over time, and is not suited for silica base material for transparent dentifrice formulation.

REFERENCE 6

A commercially available silica base material for toothpaste made in the USA was evaluated for physical properties. As a result, it was found that it had a specific surface area by the BET method of 87 m$^2$/g and by the CTAB method, of 42 m$^2$/g; and the difference in specific surface area was 45 m$^2$/g.

It proved to be a product of sufficient abrasiveness and low turbidity just after being mixed with a transparent paste vehicle, but presenting poor transparency over time.

EXAMPLE OF THIS INVENTION

Into a reactor used in reference 1 was introduced 10 kg of sodium silica solution (Na$_2$O.3.1 SiO$_2$) containing 110 g/kg of SiO$_2$ and 15 g/kg of NaCl and then under the reaction temperature kept at 90° C., 10% sulfuric acid at the flow rate of 54 g/min for 76 minutes to bring the pH of the reaction mixture to 10.0. Then the addition of 10% sulfuric acid was continued at the flow rate of 97 g/min until 14 minutes later when the pH reached 7.2. The acid was stopped and the reaction mixture was allowed to stand for ageing for 20 minutes. After repeated filtration and washing, the wet cake was dried in a hot air oven at 110° C. and finely ground.

The fine silica powder thus obtained had a specific surface area by the BET method of 36 m$^2$/g and by the CTAB method of 22 m$^2$/g and the difference in specific surface area was 14 m$^2$/g. It proved to be a product of moderate abrasiveness, good transparency and long-lasting transparency.

Table 1 shows the physical properties of the products produced above.

parent dentifrice formulations as transparency, abrasiveness and long-lasting transparency of the toothpaste product. A silica failing to satisfy said three parameters is not desirable as silica base material for toothpaste, particularly for transparent dentifrice formulation.

When the silica base material of the present invention is used in a transparent toothpaste formulation, the base material is mixed and kneaded with a transparent paste vehicle. In order to give proper fluidity to such toothpaste formulation, the paste vehicle is chosen from humectants and binders. Among humectants there are, for example, glycerine, sorbitol, polyethylene glycol, dextrin, proplylene glycol, etc., and for binders there are carboxymethyl cellulose, sodium alginate, etc. Toothpaste formulations containing such humectants or binders and other ingredients such as cleaning agent, perfume, sweetening agent, enzyme and various medicinal adjuvants are widely known to those experienced in the art.

As is understood from the explanation given, the silica base material of the present inventions is most effectively used in the production of transparent toothpaste of desired abrasiveness.

The invention will be further explained by way of examples, which in no way shall be construed to limit the scope of the invention.

In the following examples, percentages shall denote percentages by weight unless otherwise specified.

EXAMPLE 1.

Into 200 l reactor equipped with a baffle plate and an agitator with 350 mm D turbine blades was introduced 105 kg of an aqueous solution of sodium silicate (Na$_2$0.3.1 SiO$_2$) containing 100 g/kg of SiO$_2$ and 20 g/kg of NaCl and then, under the reaction temperature kept at 87° C., 10% sulfuric acid at the flow rate of 0.38 kg/min for 102 minutes to bring the pH of the reaction mixture to 10.0. Then the addition of 10% sulfuric acid was continued at the flow rate of 0.83 kg/min until 16 minutes later when the pH reached 7.1. The acid was stopped and the reaction mixture was allowed to stand for ageing for 15 minutes. After repeated filtration and washing, part of the wet cake was dried in a hot air oven at 110° C. and finely ground.

TABLE 1

| Reference | BET method specific surface area (m$^2$/g) | CTAB method specific surface area (m$^2$/g) | Difference of specific surface area (m$^2$/g) | Abrasiveness (mg) | Turbidity just after mixed | Turbidity 5 days after mixed | Refractive index |
|---|---|---|---|---|---|---|---|
| 1 | 171 | 146 | 25 | 0.3 | 0.03 | 0.06 | 1.443 |
| 2 | 215 | 98 | 117 | 0.7 | 0.38 | 0.75 | 1.448 |
| 3 | 83 | 18 | 65 | 19.8 | 0.72 | 0.93 | 1.436 |
| 4 | 208 | 21 | 187 | 34.5 | 0.92 | 0.95 | impossible to measure |
| 5 | 59 | 16 | 43 | 15.8 | 0.24 | 0.84 | 1.438 |
| 6 | 87 | 42 | 45 | 14.3 | 0.23 | 0.85 | 1.442 |
| Example of this invention | 36 | 22 | 14 | 13.8 | 0.11 | 0.12 | 1.440 |

(Remark)
Refractive index shows refractive index value immediately after mixing; turbidity shows turbidity value on refractive index immediately after mixing. The turbidity indicates the index of long-lasting transparency shown on refractive index of the fine silica powder.

As described in references Nos. 1 to 6 and the example of the present invention, three parameters of the BET specific surface area, the CTAB specific surface area and the difference in specific surface area between both methods are important factors for determining such physical properties of silica base material for trans- The fine silica powder thus obtained had a specific surface area by the BET method of 31 m$^2$/g and by the CTAB method of 15 m$^2$/g; the difference in specific surface area was 16 m$^2$/g; it had an abrasiveness value of 20.6 mg, a refractive index of 1.437 and a lowest turbidity of 0.26; and it proved to be a product of high abrasiveness and long-lasting transparency.

EXAMPLE 2

Into a 5 m³ reactor equipped with a baffle plate and an agitator with 850 mm D turbine blade was introduced 3070 kg of sodium silicate solution ($Na_2O.3.2\ SiO_2$) containing 95 g/kg of $SiO_2$ and 10 g/kg of NaCl and then, under the reaction temperature kept at 95° C., 10% sulfuric acid at the flow rate of 11.2 kg/min for 93 minutes to bring the pH of the reaction mixture to 10.0. Then the addition of 10% sulfuric acid was continued at 23.3 kg/min until 16 minutes later when the pH reached 6.7. The acid was stopped and the reaction mixture was allowed to stand for ageing for 30 minutes. After repeated filtration and washing, the obtained solid was dried in a hot air oven at 110° C. and finely ground. The fine silica powder thus obtained had a specific surface area by the BET method of 52 m²/g and by CTAB method of 19 m²/g; the difference in specific surface area was 33 m²/g; it had an abrasiveness value of 10.3 mg, a refractive index of 1.441 and a lowest turbidity of 0.08; and it proved to be a product of moderate abrasiveness and long-lasting transparency.

EXAMPLE 3

Into a 20 l reaction equipped with a baffle plate and an agitator with 150 mm D turbine blades was introduced 10 kg of an aqueous solution of sodium silicate ($Na_2O.2.8\ SiO_2$) containing 110 g/kg of $SiO_2$ and 55 g/kg of $Na_2SO_4$ and then, under the reaction temperature kept at 75° C., 11% sulfuric acid at the flow rate of 65 g/min for 64 minutes to bring the pH of the reaction mixture to 10.0. Then the addition of 11% sulfuric acid was continued at 123 g/min until 11 minutes later when the pH reached 7.6. The acid was stopped and the reaction mixture was allowed to stand for ageing for 15 minutes. After repeated filtration and washing, the obtained solid was dried in a hot air oven at 110° C. and finely ground.

The fine silica powder thus obtained had a specific surface area by the BET method of 38 m²/g and by the CTAB method of 23 m²/g; the difference in specific surface area was 15 m²/g; it had an abrasiveness value of 17.8 mg, a refractive index of 1.436 and a lowest turbidity of 0.16; and it proved to be a product of moderate abrasiveness and long-lasting transparency.

EXAMPLE 4

Into a reactor used in example 3 was introduced 10 kg of an aqueous solution of potassium silicate ($K_2O\ 3.0\ SiO_2$) containing 100 g/kg of $SiO_2$ and 13 g/kg of KCl and then, under the reaction temperature kept at 80° C., 8% hydrochloric acid at the flow rate of 78 g/min for 46 minutes to bring the of the reaction mixture to 10.0. Then the pH addition of 8% hydrochloric acid was continued at 133 g/min until 9 minutes later when the pH reached 6.8. The acid was stopped and the reaction mixture was allowed to stand for ageing for 20 minutes. After repeated filtration and washing, the obtained solid was dried in a hot air oven at 110° C. and finely ground.

The fine silica powder thus obtained had a specific surface area by the BET method of 53 m²g and by the CTAB method of 42 m²/g; the difference in specific surface area of both method was 11 m²/g; it had an abrasiveness value of 6.8 mg, a refractive index of 1.442 and a lowest turbidity of 0.04; and it proved to be a product of moderate abrasiveness and good transparency and long-lasting transparency.

The examples given above clearly show that the product of the present invention has excellent characteristics as a base material for transparent dentifrice formulations.

It has been proved that when there is a need to add good transparency and long-lasting transparency to silica base materials having comparatively high abrasiveness, the use of humectant selected from sorbitol and polyethylene glycol together with water gives excellent results for such requirement.

Table 2 below shows refractive index and long-lasting transparency measured on the glycerin solution, sorbitol solution and polyethylene glycol solution, each containing 30% of silica base materials obtained in Example 1.

TABLE 2

| Humectant | Turbidity Just after mixed | Turbidity 100 days after mixed | Refractive index |
|---|---|---|---|
| glycerin aqueous solution | 0.26 | 0.38 | 1.437 |
| sorbitol aqueous solution | 0.13 | 0.13 | 1.437 |
| polyethylene glycol aqueous solution | 0.11 | 0.13 | 1.437 |

Remark: Turbidity measured after being kept for 100 days at 50° C.

As shown in Table 2, glycerin solution humectant has a drawback in causing slight loss of transparency during a long storage period while sorbitol solution and polyethylene glycol solution bring out no change in transparency during a long storage period. This proves that transparent toothpaste composed of silica base materials of this invention, a humectant selected from sorbitol and polyethylene glycol and water far excells in transparency of the toothpaste product and its long-lasting transparency.

REFERENCE EXAMPLE 1

The refractive index and turbidity of commercial transparent toothpastes are as shown in Table 3.

TABLE 3

| Commercial transparent toothpaste | Refractive index | Turbidity |
|---|---|---|
| Brand A | 1.443 | 0.658 |
| Brand B | 1.448 | 0.657 |

Comparison of Table 3 and other data cited hereinbefore reveals clearly that the transparent toothpaste formulations now commercially available are substantially less transparent than the corresponding formulations using the silica base material of the present invention.

We claim:

1. A method for the production of a silica base material for a dentifrice formulation, which comprises reacting an alkali metal silicate solution and hydrochloric or sulfuric acid in the presence of an electrolyte by adding the acid to the silicate solution in two stages, a silica crystallization stage for which the pH of the reaction mixture is brought to 10.0, and a neutralization stage during which the pH is finally brought down to 8.0–6.5, wherein the ratio of the rate of addition of chloride added as hydrochloric acid or sulfate added as sulfuric acid in said neutralization stage to said rate of addition in the crystallization stage is at least 5:3, and the neutralization is carried out within 30 minutes; and ageing the neutralized reaction mixture for at least 10 minutes, said silica base material having a specific surface area by the BET method of 5-60 m$^2$/g-anhydride, and by the CTAB method of 5-60 m$^2$/g-anhydride; having a difference in specific surface area of less than 40 m$^2$/g-anhydride between the BET method and the CTAB method; and having a refractive index of 1.42-1.45.

2. The method described in claim 1, where the electrolyte has previously been added to the alkali metal silicate solution.

3. The method described in claim 1, where the SiO$_2$ concentration of the alkali metal silicate solution before the addition of hydrochloric or sulfuric acid is 5-15% by weight.

4. The method described in claim 1, where the electrolyte is alkali metal salt of a mineral acid.

5. The method described in claim 1, where the amount of the electrolyte is 10-60% by weight of SiO$_2$.

6. The method described in claim 1, where the concentration of hydrochloric or sulfuric acid is 5-15% by weight.

7. The method described in claim 1, where the reaction temperature during the silica crystallization stage is 60°-100° C.

8. The method described in claim 1, where the addition of hydrochloric or sulfuric acid during the silica crystallization stage is conducted to take 40 minutes to 4 hours.

9. The method described in claim 1, wherein the alkali metal silicate solution has a molar ratio, SiO$_2$/X$_2$O of 2-4 wherein X denotes alkali metal.

* * * * *